(12) United States Patent
Youssef

(10) Patent No.: US 10,197,488 B2
(45) Date of Patent: Feb. 5, 2019

(54) SYSTEMS AND METHODS FOR DETECTING CHIPS IN FLUID OF AIRCRAFT ENGINE

(71) Applicant: PRATT & WHITNEY CANADA CORP., Longueuil (CA)

(72) Inventor: Michael Youssef, Mississauga (CA)

(73) Assignee: PRATT & WHITNEY CANADA CORP., Longueuil (CA)

( * ) Notice: Subject to any disclaimer, the term of this patent is extended or adjusted under 35 U.S.C. 154(b) by 100 days.

(21) Appl. No.: 15/623,460

(22) Filed: Jun. 15, 2017

(65) Prior Publication Data

US 2018/0364141 A1    Dec. 20, 2018

(51) Int. Cl.
*G01R 31/08*    (2006.01)
*G01N 15/06*    (2006.01)
(Continued)

(52) U.S. Cl.
CPC ......... *G01N 15/0656* (2013.01); *F01M 11/10* (2013.01); *G01N 27/74* (2013.01); *G01N 33/2858* (2013.01); *G01V 3/102* (2013.01)

(58) Field of Classification Search
CPC ... G01N 2015/1497; G01N 2021/6419; G01N 2021/6421; G01N 2021/6478; G01N 2021/6491; G01N 2021/7786; G01N 2021/825; G01N 2033/184; G01N 2033/4975; G01N 2035/00158; G01N 2035/00564; G01N 21/253; G01N 21/5907; G01N 21/71; G01N 21/7703; G01N 21/78; G01N 21/94; G01N 21/956; G01N 2201/0628; G01N 2201/068; G01N 2201/101; G01N 2458/10; G01N 2520/00; G01N 27/025; G01N 27/041; G01N 27/06;
(Continued)

(56) References Cited

U.S. PATENT DOCUMENTS 3,432,750 A * 3/1969 Botstiber ........... G01N 15/0656
200/61.09
4,100,491 A * 7/1978 Newman, Jr. ............ G01V 3/08
200/61.09
(Continued)

FOREIGN PATENT DOCUMENTS

WO    WO2010078555    7/2010

*Primary Examiner* — Vinh P Nguyen
(74) *Attorney, Agent, or Firm* — Norton Rose Fulbright Canada LLP

(57) ABSTRACT

There is described herein methods and systems for detecting electrically-conductive particles (chips) in fluid of an aircraft engine. The method comprises applying a plurality of excitation currents $I_i$ across a magnetic chip detector mounted to a fluid system of the aircraft engine and measuring a corresponding plurality of resistance values $R_i$, where i is an integer that varies from 1 to N, and where N corresponds to a number of different excitation currents applied across the magnetic chip detector. The method further comprises determining a chip size indication Y from the plurality of resistance values $R_i$, and detecting a chip in the fluid when the chip size indication Y exceeds a threshold $Y_{thres}$.

20 Claims, 4 Drawing Sheets

(51) Int. Cl.
*G01N 27/74* (2006.01)
*G01N 33/28* (2006.01)
*F01M 11/10* (2006.01)
*G01V 3/10* (2006.01)

(58) Field of Classification Search
CPC .. G01N 27/30; G01N 27/3272; G01N 27/447; G01N 33/1866; G01N 33/1893; G01N 33/22; G01N 33/2858; G01N 33/487; G01N 33/48721; G01N 33/497; G01N 33/54333; G01N 33/5438; G01N 35/08; G01R 33/1269; G01R 33/09; G01R 33/12; G01R 33/1276; G01R 33/093; G01R 31/005; G01R 31/008; G01R 31/026; G01V 3/08
See application file for complete search history.

(56) References Cited

U.S. PATENT DOCUMENTS

| | | |
|---|---|---|
| 4,219,805 A | 8/1980 | Magee et al. |
| 5,663,642 A | 9/1997 | Rumberger et al. |
| 6,445,177 B1 * | 9/2002 | Higgins ............ B03C 1/286 |
| | | 324/204 |
| 7,886,975 B2 * | 2/2011 | Matsuo ............ G06K 17/0022 |
| | | 235/439 |
| 8,522,604 B2 | 9/2013 | Zhe et al. |

* cited by examiner

SYSTEMS AND METHODS FOR DETECTING CHIPS IN FLUID OF AIRCRAFT ENGINE

TECHNICAL FIELD

The disclosure relates generally to aircraft engine operation and more particularly to the detection of electrically-conductive particles (chips) in fluid of aircraft engines.

BACKGROUND OF THE ART

Magnetic chip detectors are generally mounted to a fluid system of an aircraft engine to assess the presence or absence of metallic chips in the fluid. The metallic chips may result from normal engine wear and tear and/or major engine failures, which causes metal chips to break loose from engine parts and circulate in the engine fluid.

Some magnetic chip detectors have two spaced-apart magnetic prongs positioned in the fluid such that, when attracted metallic chips bridge the gap between the two prongs, an electronic circuit of the magnetic chip detector is closed which may cause an indication in the cockpit of the aircraft to be activated. Other magnetic chip detectors have only one magnet and the gap to be bridged is between the magnet and a housing.

As the presence of metal chips in engine fluid is indicative of engine condition, there exists a need to improve on chip detection for aircraft engines.

SUMMARY

In accordance with one aspect, there is provided a method for detecting electrically-conductive particles (chips) in fluid of an aircraft engine. The method comprises applying a plurality of excitation currents $I_i$ across a magnetic chip detector mounted to a fluid system of the aircraft engine and measuring a corresponding plurality of resistance values $R_i$, where i is an integer that varies from 1 to N, and where N corresponds to a number of different excitation currents applied across the magnetic chip detector. The method comprises determining a chip size indication Y from the plurality of resistance values $R_i$, and detecting a chip in the fluid when the chip size indication Y exceeds a threshold $Y_{thres}$.

In accordance with another aspect, there is provided a detection system for an aircraft engine, for detecting electrically-conductive particles (chips). The detection system comprises a processing unit, and a non-transitory memory communicatively coupled to the processing unit and comprising computer-readable program instructions being executable by the processing unit for causing a plurality of excitation currents $I_i$ to be applied across a magnetic chip detector mounted to a fluid system of the aircraft engine and receiving a corresponding plurality of resistance values $R_i$, where i is an integer that varies from 1 to N, and where N corresponds to a number of different excitation currents applied across the magnetic chip detector, determining a chip size indication Y from the plurality of resistance values $R_i$, and detecting a chip in the fluid when the chip size indication Y exceeds a threshold $Y_{thres}$.

It is noted that in this disclosure, the expression "chip size" is similar to the expression "chip quantity" and both expressions can be used interchangeably. Correspondingly, the expressions "chip size indication Y" and "chip quantity indication Y" can also be used interchangeably.

DESCRIPTION OF THE DRAWINGS

Reference is now made to the accompanying figures in which.

It will be noted that throughout the appended drawings, like features are identified by like reference numerals.

DETAILED DESCRIPTION

Knowledge of the size or quantity of metal chips that are present in the fluid is used to manage operation of an aircraft engine. Large metal chips can indicate or cause a major engine failure and can require immediate aircraft operator action (e.g., shutdown engine during flight), while small metal chips (often called "fuzz") are typically caused by normal engine wear and tear, and action can be delayed to the next maintenance interval.

There is described herein methods and systems for detecting metallic chips in a fluid system of an aircraft engine. The chip is detected based on the measurement of a plurality of resistance values $R_i$ obtained while applying a corresponding plurality of excitation currents $I_i$ across a magnetic chip detector mounted to the fluid system of the aircraft engine. A chip size indication Y can then be determined from the plurality of resistance values $R_i$, thus allowing a chip to be detected in the fluid when the chip size indication Y exceeds a threshold $Y_{thres}$.

Figure 1:
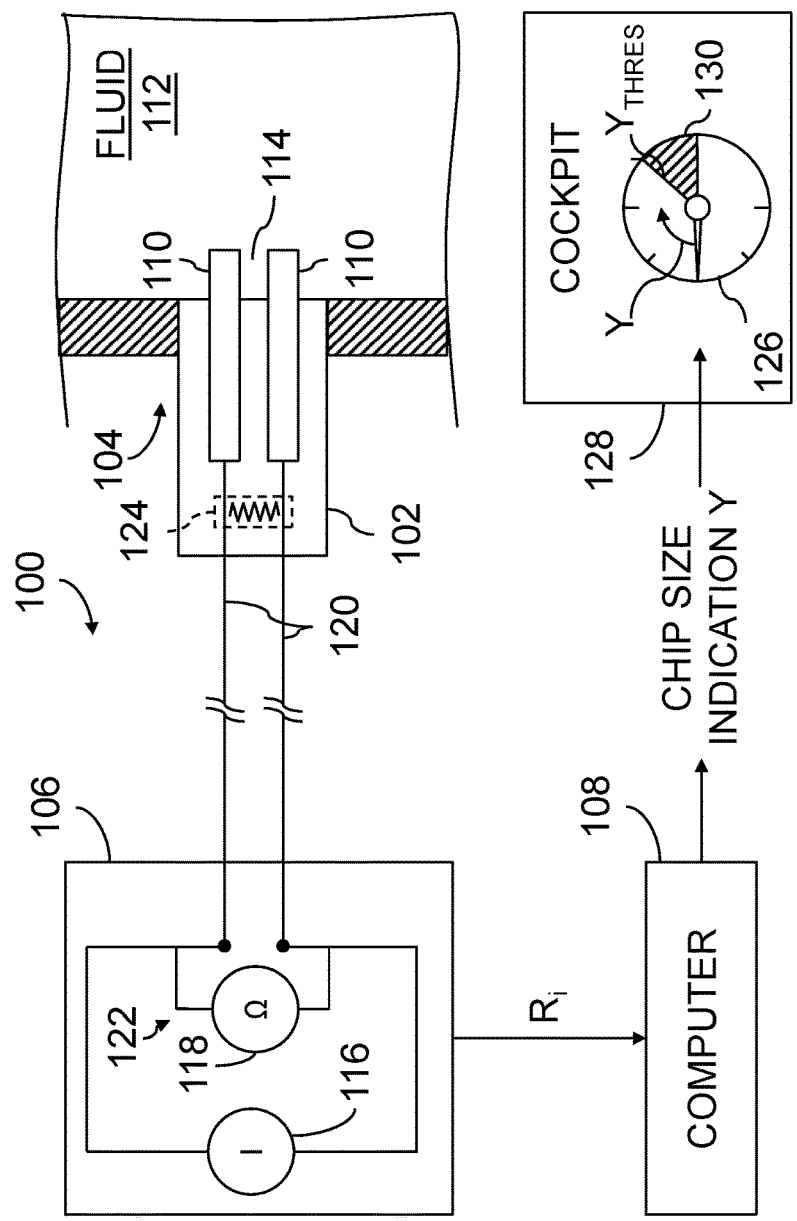
FIG. 1 is a schematic view of an example chip detection system for an aircraft engine.

With reference to FIG. 1, there is illustrated a chip detection system 100 for an engine of an aircraft. The aircraft may be any type of aircraft with an engine, such as a fixed-wing aircraft, a rotary-wing aircraft, and a jet aircraft. The engine may be any type of internal combustion engine, such as gas turbine engines, jet engines, and the like. For example, the engine may be a turbofan engine, a turboprop engine, or a turboshaft engine. Other engines may also apply.

As depicted, the chip detection system 100 has a magnetic chip detector 102 mounted to a fluid system 104 of the aircraft engine, a resistance measurement circuit 106, and a computer 108, which may be any type of computing device having processing capabilities.

In the example illustrated, the magnetic chip detector 102 has two magnetic prongs 110 positioned in fluid 112 of the fluid system 104. In some embodiments, the fluid system 104 may be an oil system in which case the fluid 112 is oil. However, other embodiments may also apply.

The magnetic chip detector 102 may be provided near a gearbox, near a pump or at any other suitable location in the fluid system 104. The two magnetic prongs 110 are spaced-apart by a gap 114 such that when one or more metallic chips ("the chip") bridge the gap 114, electricity can be conducted from one magnetic prong to the other. As it will be understood, any type of magnetic chip detector can be used. For instance, the magnetic chip detector 102 can have a single magnetic prong (for example where a gap lies between the single prong and a magnetic housing) or more than two magnetic prongs. In one example, each magnetic prong may have a sixteenth of an inch in diameter, and the gap may be of three sixteenth of an inch. In another example, each magnetic prong may have $\frac{1}{32}$ of an inch in diameter, and the gap may be of $\frac{1}{32}$ of an inch. In some embodiments, the diameter of the magnetic prong may range between $\frac{1}{64}$ of an inch to ⅛ of an inch, and the gap may range between ¹⁄₆₄ of an inch and ⅛ of an inch. Other dimensions may also be used.

As shown, the resistance measurement circuit 106 has an excitation current source 116 adapted to apply a plurality of excitation currents $I_i$ across the magnetic chip detector 102, and an ohmmeter 118 adapted to measure a corresponding plurality of resistance values $R_i$. Each resistance value $R_i$ is indicative of the electrical resistance across the gap 114 of the magnetic chip detector 102 when a corresponding excitation current $I_i$ is applied across the gap 114 of the magnetic chip detector 102.

The variable i is an integer that varies from 1 to N, where N corresponds to a number of different excitation currents applied across the magnetic chip detector 102. Accordingly, a first resistance value $R_1$ can be measured when a first excitation current $I_1$ is applied across the magnetic chip detector 102, a second resistance value $R_2$ can be measured when a second excitation current $I_2$ is applied across the magnetic chip detector 102, and so forth.

In the example illustrated in FIG. 1, the excitation current source 116 is independent of the computer 108, but in alternative embodiments, the excitation current source 116 can be controlled by the computer 108.

In some embodiments, the ohmmeter 118 has a voltmeter adapted to measure a corresponding plurality of voltage values $V_i$ which are then converted into the corresponding plurality of resistance values $R_i$ by the equation $R_i=V_i/I_i$ according to Ohm's Law.

In the illustrated embodiment, the resistance measurement circuit 106 is connected to the magnetic chip detector 102 via conductors 120. More specifically, both the excitation current source 116 and the ohmmeter 118 are connected to the two magnetic prongs 110 of the magnetic chip detector 102 via the conductors 120. The ohmmeter 118 is connected to a circuit 122 including one or more electrical resistors ("the resistor 124") connected in parallel with the two magnetic prongs 110 and across the conductors 120. Such a parallel connection between the resistor 124 and the magnetic chip detector 102 allows electricity to be conducted across the circuit 122 independently of whether or not the gap 114 is bridged by a chip.

In some embodiments, the resistor 124 is internal to the magnetic chip detector 102. However, the resistor 124 can be external to the magnetic chip detector 102. For instance, the resistor 124 can be internal to the resistance measurement circuit 106. The resistor 124 may vary due to design. In alternate embodiments, the resistor 124 is omitted.

As illustrated, the computer 108 is operatively connected to the resistance measurement circuit 106 to further process the measured resistance values $R_i$ to determine a chip size indication Y.

Figure 2:
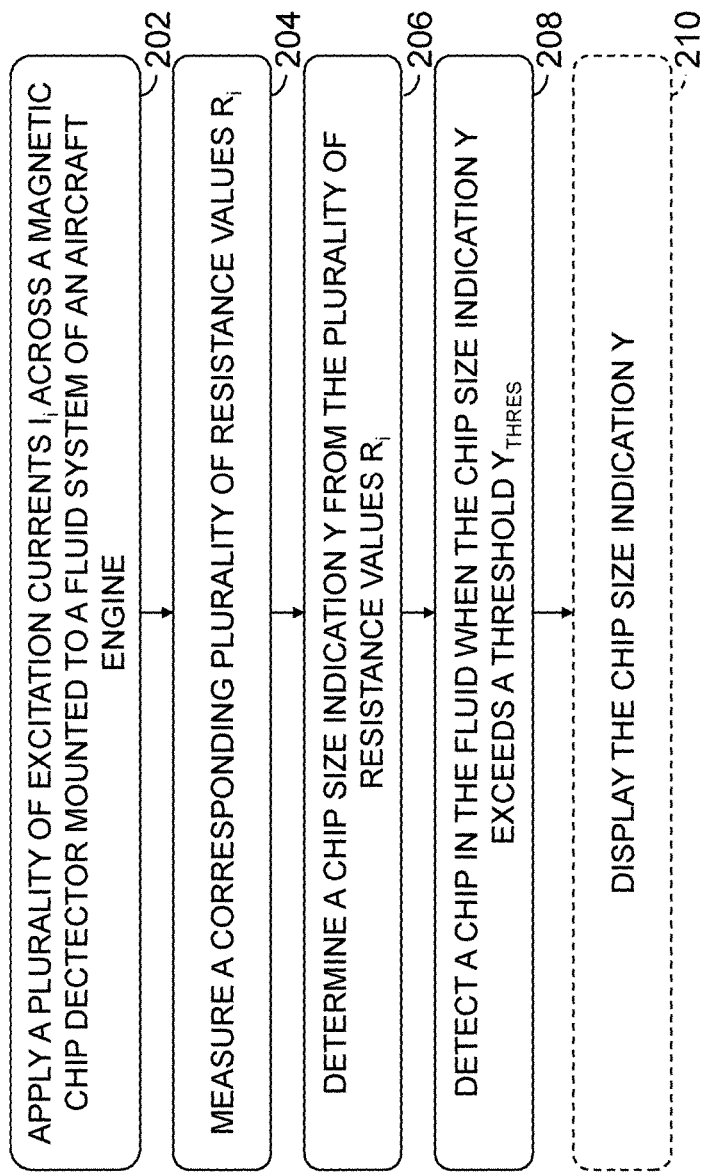
FIG. 2 is a flow chart of an example method for detecting chips in fluid of the chip detection system of FIG. 1.

FIG. 2 shows a flow chart of an exemplary method 200 for detecting chips in fluid of the aircraft engine. As it will be understood, the method 200 can be performed continuously or periodically as the aircraft engine is running. In some embodiments, the method 200 is performed upon receipt of an external request, for example from a pilot input. In some embodiments, the method 200 is performed automatically at regular or irregular intervals. A trigger to perform the method 200 may be received from an engine control system, an aircraft control system, or any other operating system of the engine/aircraft. FIG. 2 will be described with reference to FIG. 1.

At step 202, a plurality of excitation currents $I_i$ are applied across the magnetic chip detector 102, for example using the excitation current source 116 of the resistance measurement circuit 106.

In some embodiments, the plurality of excitation currents $I_i$ are applied by varying a continuous excitation current successively across a range spanning the plurality of excitation currents $I_i$. In these embodiments, the resistance measurement circuit 106 can scan a range of excitation currents at specific intervals. For instance, the resistance measurement circuit 106 can perform a continuous scan across a range of excitation currents ranging between 0.1 mA and 25 mA at the following specific intervals: 0.1 mA, 0.25 mA, 0.5 mA, 1 mA, 5 mA, 10 mA and 25 mA. These intervals are non-limiting examples, the intervals at which the excitations currents are continuously scanned can be different. Similarly, the range of excitation currents of the continuous scan can be different. The resistance measurement circuit 106 can be adapted to repeat the continuous scan at an adjustable frequency, such that the scan can be performed for a plurality of frequencies. Examples of frequencies comprise 1 Hz to 10 Hz. For instance, the continuous scan can be performed at 10 times per second.

In some embodiments, the plurality of excitation currents $I_i$ are applied by varying the excitation current in discrete current values successively across a range spanning the plurality of excitation currents $I_i$. In these embodiments, the resistance measurement circuit 106 can apply a range of discrete excitation currents at specific intervals. For instance, the resistance measurement circuit 106 can apply discrete excitation currents across a range of excitation currents ranging between 0.1 mA and 25 mA at the following specific intervals: 0.1 mA, 0.25 mA, 0.5 mA, 1 mA, 5 mA, 10 mA and 25 mA. These intervals are non-limiting examples, the intervals at which the discrete excitation currents are applied can be different. Similarly, the range of discrete excitation currents can be different. The resistance measurement circuit 106 can be adapted to repeatedly apply the discrete excitation currents at an adjustable frequency, such that the application of the discrete excitation currents can be performed for a plurality of frequencies. Examples of frequencies comprise 1 Hz to 10 Hz. For instance, the discrete excitation currents can be applied at a frequency of 10 times per second.

In some embodiments, the plurality of excitation currents $I_i$ can be applied via a combination of varying a continuous excitation current across a portion of the range spanning the plurality of excitation currents $I_i$ and applying discrete excitation currents across a complementary portion of the range spanning the plurality of excitation currents $I_i$.

At step 204, a plurality of resistance values $R_i$ are measured across the chip detector, for example using the resistance measurement circuit 106. At least one resistance value $R_i$ is obtained for each applied excitation current $I_i$. Multiple resistance readings may be taken for each applied excitation current $I_i$ and an average resistance value $R_i$ may be determined from the multiple resistance readings.

In some embodiments, the computer 108 is connected to the resistance measurement circuit 106 in a manner that allows the computer 108 to read the resistance values $R_i$ directly from the resistance measurement circuit 106. In other embodiments, the computer 108 and the resistance measurement circuit 106 are integrated as a single device. Also alternatively, the resistance measurement circuit 106 comprises a processing unit capable of reading and interpreting the measured resistance values $R_i$.

At step 206, a chip size indication Y is determined from the plurality of resistance values $R_i$. The chip size indication may be determined by the computer 108, a processing unit internal to the resistance measurement circuit 106, or any other computing device.

In some embodiments, the chip size indication Y is indicative of the size of a single chip bridging the gap 114 whereas, in some other embodiments, the chip size indication is indicative of the size of a plurality of chips bridging the gap 114. As mentioned above, the chip size indication Y can also be indicative of the quantity of chips bridging the gap 114.

In an example embodiment, the chip size indication Y is determined by summing the plurality of resistance values $R_i$ together to obtain the chip size indication Y. An example is described with reference to Table 1 presented hereinbelow, which illustrates examples of excitation currents $I_i$ and corresponding resistance values $R_i$, where i varies from 1 to 7.

TABLE 1

| i | Excitation current values $I_i$ (mA) | Resistance values $R_i$ (Ω) |
|---|---|---|
| 1 | 0.1 | 500 |
| 2 | 0.25 | 400 |
| 3 | 0.5 | 300 |
| 4 | 1 | 200 |
| 5 | 5 | 100 |
| 6 | 10 | 50 |
| 7 | 25 | 25 |

In the example of Table 1, the chip size indication Y is determined by summing the plurality of resistance values $R_1$ to $R_7$. More specifically, the following mathematical operation is performed: $\Sigma_{i=1}^{N=7} R_i = R_1+R_2+R_3+R_4+R_5+R_6+R_7 = 1575\Omega$. As per step 208, a chip is detected in the fluid when the chip size indication Y exceeds a threshold $Y_{thres}$. For instance, in a case where the threshold $Y_{thres}$ is 1500Ω, and upon determining that the chip size indication Y is 1575Ω, a chip is detected in the fluid.

In some embodiments, the chip size indication Y is determined by applying weighting factors $X_i$ to the plurality of resistance values $R_i$ and summing the weighted resistance values $X_i R_i$ together to obtain the chip size indication Y. An example is described with reference to Table 2 presented hereinbelow, showing examples of excitation currents $I_i$, corresponding resistance values $R_i$ and corresponding weighting factors $X_i$, where the integer i varies from 1 to 7.

TABLE 2

| i | Excitation current values $I_i$ (mA) | Resistance values $R_i$ (Ω) | Weighting factors $X_i$ (1/Ω) |
|---|---|---|---|
| 1 | 0.1 | 500 | 0 |
| 2 | 0.25 | 400 | 0.5 |
| 3 | 0.5 | 300 | 0.6 |
| 4 | 1 | 200 | 0.7 |
| 5 | 5 | 100 | 1 |
| 6 | 10 | 50 | 1 |
| 7 | 25 | 25 | 1 |

In the example of Table 2, the chip size indication Y is determined by weighting the resistance values $R_i$ with a corresponding one of the weighting values $X_i$. More specifically, the following mathematical operation may be performed: $\Sigma_{i=1}^{N=7} X_i R_i = X_1 R_1 + X_2 R_2 + X_3 R_3 + X_4 R_4 + X_5 R_5 + X_6 R_6 + X_7 R_7 = 695$. As per step 208, a chip is detected in the fluid when the chip size indication Y exceeds the threshold $Y_{thres}$. For instance, in a case where the threshold $Y_{thres}$ is 500, and upon determining that the chip size indication Y is 695, a chip is detected in the fluid.

In some embodiments, the weighting factors $X_i$ can be used to avoid detection of nuisance chips. Nuisance chips may be defined as having a size below a given value. The value may be determined by a manufacturer of a fluid system, a manufacturer of an engine, a manufacturer of an aircraft, or any other party. For example, a nuisance chip may be deemed to be any chip having a size less than or equal to 0.004 inches. In another example, nuisance chips are defined as having a size less than or equal to 0.007 inches, or 0.009 inches. Simulations and/or testing may be used to determine the optimum cut-off size for nuisance chips. In some embodiments, the optimum cut-off size is set as a function of one or more parameter, such as engine type, fluid type, fluid system type, operating conditions of the engine, and the like.

In some embodiments, the weighting factors $X_i$ can be used to ensure detection of chips having a target size. For example, it may be desired to detect chips having a size equal to or greater than 0.010 inches, 0.015 inches, 0.020 inches, or any other size deemed to cause issues to the engine and/or fluid system to which the method is applied. This may, for example, be useful to avoid excessive maintenance action and customer delays. Simulations and/or testing may be used to determine the target size for chip detection. In some embodiments, the target size is set as a function of one or more parameter, such as engine type, fluid type, fluid system type, operating conditions of the engine, and the like.

In some embodiments, the weighting factors are used to avoid detection of nuisance chips and to ensure detection of chips of a target size. Smaller excitation currents $I_i$ are less sensitive to smaller chips and greater excitation currents $I_i$ are more sensitive to smaller chips. Therefore, the weight values may be set accordingly as a function of a desired sensitivity level and/or target. Similarly, the excitation currents $I_i$ may also be set accordingly. The weighting factors $X_i$ and/or excitation currents $I_i$ can be adjusted through software to modify the sensitivity of the chip detection system 100.

Optimal weighting factors $X_i$ for a given application can be obtained through testing in the development phase of the aircraft engine and be used thereafter during the lifetime of the aircraft engine. Alternatively, any one of the weighting factors $X_i$ may be modified to increase the sensitivity as the engine or aircraft operates over time. The sensitivity at which the chip detection system 100 detects chips in the fluid 112 can be modified dynamically by modifying the threshold $Y_{thres}$.

As can be seen from Table 2, some of the weighting factors $X_i$ can be identical whereas others of the weighting factors $X_i$ can be different. In some embodiments, weighting factors $X_i$ can be different for each one of the plurality of resistance values $R_i$.

One or more of the weighting factors $X_i$ can be null so as to ignore one or more of the resistance values $R_i$ to the benefit of other ones of the resistance values $R_i$. For instance, the weighting factor $X_1$ in Table 2 is null. In this case, the resistance value $R_1$, measured using the excitation current $I_1$ of 0.1 mA, is ignored. In alternate embodiments, all of the weighting factors $X_i$ except one can be null. The weighting factors $X_i$ may be stored on a computer-readable memory which is accessible by the computer 108.

In some embodiments, a plurality of sets of weighting factors $X_i$ associated with the aircraft engine are stored. For instance, an input can be received from the aircraft engine, the aircraft and/or any suitable remote device such that one of the sets of weighting factors $X_i$ can be selected based on the input. Examples of such input comprise a type of the aircraft engine, an oil type, an oil flow rate, a rotational speed of the aircraft engine, a capture rate of the magnetic chip detector, a size or quantity of the chip to detect or any combination thereof. The selection of the weighting factors $X_i$ can allow the measured resistance values $R_i$ to be weighted according to one or more inputs of the aircraft engine. In some embodiments, one or more thresholds $Y_{thres}$ are stored such that one of the thresholds $Y_{thres}$ can be selected based on the received input.

In some embodiments, the method 200 comprises a step 210 of displaying the chip size indication Y on an aircraft instrument, such as on a gauge 126 of a cockpit 128, as shown in FIG. 1. In some embodiments, the numerical value of the chip size is displayed using a gauge or an LCD display. Any other suitable type of display may be used, such as a liquid crystal display, an electronic paper display, a cathode ray tube display, an electroluminescent display, and the like.

Although shown as part of the cockpit 128 of the aircraft, the display may be located anywhere in the aircraft. In some embodiments, the chip size indication Y is sent via a wired connection between the computer 108 and the aircraft instrument. A wireless connection between the computer 108 and the aircraft display 126 may also be used.

In some embodiments, the gauge 126 or other visual indicator of chip size may comprise the threshold $Y_{thres}$ and the visual indicator displays the chip size indication Y as being above or below the threshold $Y_{thres}$ For example, the threshold $Y_{thres}$ can be defined by a zone 130 on the gauge 126. Alternatively, the visual indicator is modified, such as in color, size, or shape, when the chip size indication Y exceeds the threshold $Y_{thres}$. Other embodiments for displaying chip size indication Y along a scale and updating in real-time can also be used.

In some embodiments, the display of the chip size indication Y can be separated in three categories: small, medium, and critical based on a number M of thresholds $Y_{thres,k}$, where k is an integer varying from 1 to M. A first threshold $Y_{thres,1}$ can differentiate a medium chip size indication from a critical chip size indication, and a second threshold $Y_{thres,2}$, smaller than the first threshold $Y_{thres,1}$, can differentiate a small chip size indication from a medium chip size indication. In this embodiment, the displaying may comprise activating a green LED when the chip size indication Y is small (i.e. the chip size indication is below the second threshold $Y_{thres,2}$), the displaying can comprise activating a yellow LED when the chip size indication Y is medium (i.e. the chip size indication Y is between the second threshold $Y_{thres,2}$ and the first threshold $Y_{thres,1}$) and displaying may comprise activating a red LED when the chip size indication is critical (i.e. the chip size exceeds the first threshold $Y_{thres,1}$). Immediate maintenance actions can follow a red LED activation whereas an inspection can be recommended following a yellow LED activation. In these embodiments, the weighting factors $X_i$ can be adjusted to provide a chip size indication Y varying between a lower limit value $Y_{min}$ and an upper limit value $Y_{max}$, where the first and second thresholds $Y_{thres,1}$ and $Y_{thres,2}$ are comprised between the lower limit value $Y_{min}$ and the upper limit value $Y_{max}$. For instance, the lower limit value $Y_{min}$ can be adjusted to 0 and the upper limit value $Y_{max}$ can be adjusted to 1000, in which case the first threshold can be $Y_{thres,1}=500$ and the second threshold $Y_{thres,2}=200$. The display of the chip size indication Y can be separated into more or less than three categories, depending on the embodiments.

In some embodiments, the measured resistance values $R_i$ are continuously stored in the computer 108 and/or transmitted to an external server/computer for health monitoring, trending and/or analysis. Storing the resistance values $R_i$, and the corresponding excitation currents $I_i$, can allow monitoring of the resistance values $R_i$ over time.

In alternate embodiments, a warning indicative of a chip in the fluid 112 may also be issued when the chip size indication Y exceeds the threshold $Y_{thres}$. For instance, the threshold $Y_{thres}$ can be set to 500. Accordingly, in this specific embodiment, a warning indicative of a chip in the fluid 122 may be issued when the chip size indication Y is above 500. This exemplary threshold is provided as an example only. Other engines or installations may have other thresholds.

In some embodiments, the resistance values $R_i$ and the chip size indication Y are monitored over time. In these embodiments, a gradual increase in the chip size indication Y can indicate the gradual accumulation of small chips (e.g., from normal engine wear and tear) whereas a sudden increase in the chip size indication Y can indicate the presence of a large chip (e.g., from a major engine failure). In this specific embodiment, the warning is issued when the chip size indication Y is such that the working of the aircraft engine may be altered.

In other embodiments, the warning is issued directly in the aircraft to the pilot(s) and/or the flight crew. This may be the case, for instance, when the magnetic chip detector 102 is positioned at a key location in the fluid system 104. In such embodiments, the warning may be embodied by activating a light in the cockpit or elsewhere in the aircraft. The warning may also be audible, or some other form of visual warning, such as text or graphic on a display. Other embodiments may also apply.

In some other embodiments, the magnetic chip detector 102 allows the warning to be issued to a computer-readable memory for storing thereof. In this case, the first warning may be accessed during maintenance of the aircraft engine.

Figure 3:
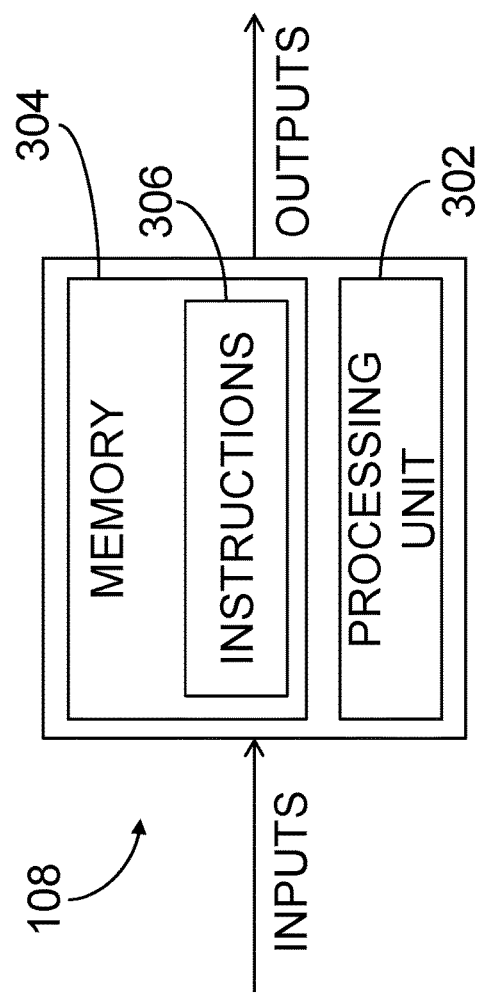
FIG. 3 is a block diagram of an example computer device for implementing the method of FIG. 2.

FIG. 3 shows a schematic representation of the computer 108, as a combination of software and hardware components. In this example, the computer 108 is illustrated with one or more processing units (referred to as "the processing unit 302") and one or more computer-readable memories (referred to as "the memory 304") having stored thereon program instructions 306 configured to cause the processing unit 302 to generate one or more outputs based on one or more inputs. The inputs may comprise one or more signals representative of the excitation currents $I_i$, the measured resistance values $R_i$, the threshold(s) $Y_{thres}$, one or more sets of weighting factors $X_i$ and the like. The outputs may comprise one or more signals representative of the chip size indication Y, the warning and the like.

The processing unit 302 may comprise any suitable devices configured to cause a series of steps to be performed so as to implement the computer-implemented method 200 such that the instructions 306, when executed by the computer 108 or other programmable apparatuses, may cause the functions/acts/steps specified in the methods described herein to be executed. The processing unit 302 may comprise, for example, any type of general-purpose microprocessor or microcontroller, a digital signal processing (DSP) processor, a central processing unit (CPU), an integrated circuit, a field programmable gate array (FPGA), a reconfigurable processor, other suitably programmed or programmable logic circuits, or any combination thereof.

The memory 304 may comprise any suitable known or other machine-readable storage medium. The memory 304 may comprise non-transitory computer readable storage medium such as, for example, but not limited to, an electronic, magnetic, optical, electromagnetic, infrared, or semiconductor system, apparatus, or device, or any suitable combination of the foregoing. The memory 304 may comprise a suitable combination of any type of computer memory that is located either internally or externally to device such as, for example, random-access memory (RAM), read-only memory (ROM), compact disc read-only memory (CDROM), electro-optical memory, magneto-optical memory, erasable programmable read-only memory (EPROM), and electrically-erasable programmable read-only memory (EEPROM), Ferroelectric RAM (FRAM) or the like. Memory 304 may comprise any storage means (e.g., devices) suitable for retrievably storing machine-readable instructions executable by the processing unit 302.

Each computer program described herein may be implemented in a high level procedural or object oriented programming or scripting language, or a combination thereof, to communicate with a computer. Alternatively, the programs may be implemented in assembly or machine language. The language may be a compiled or an interpreted language. Computer-executable instructions may be in many forms, including program modules, executed by one or more computers or other devices. Generally, program modules comprise routines, programs, objects, components, data structures, etc., that perform particular tasks or implement particular abstract data types. Typically the functionality of the program modules may be combined or distributed as desired in various embodiments.

In some embodiments, the computer 108 is provided in the form of an engine computer of the aircraft engine. Such an engine computer can comprise any engine controlling devices such as an engine control unit (ECU), an engine electronic controller (EEC), an engine electronic control system, and a Full Authority Digital Engine Controller (FADEC).

Figure 4:
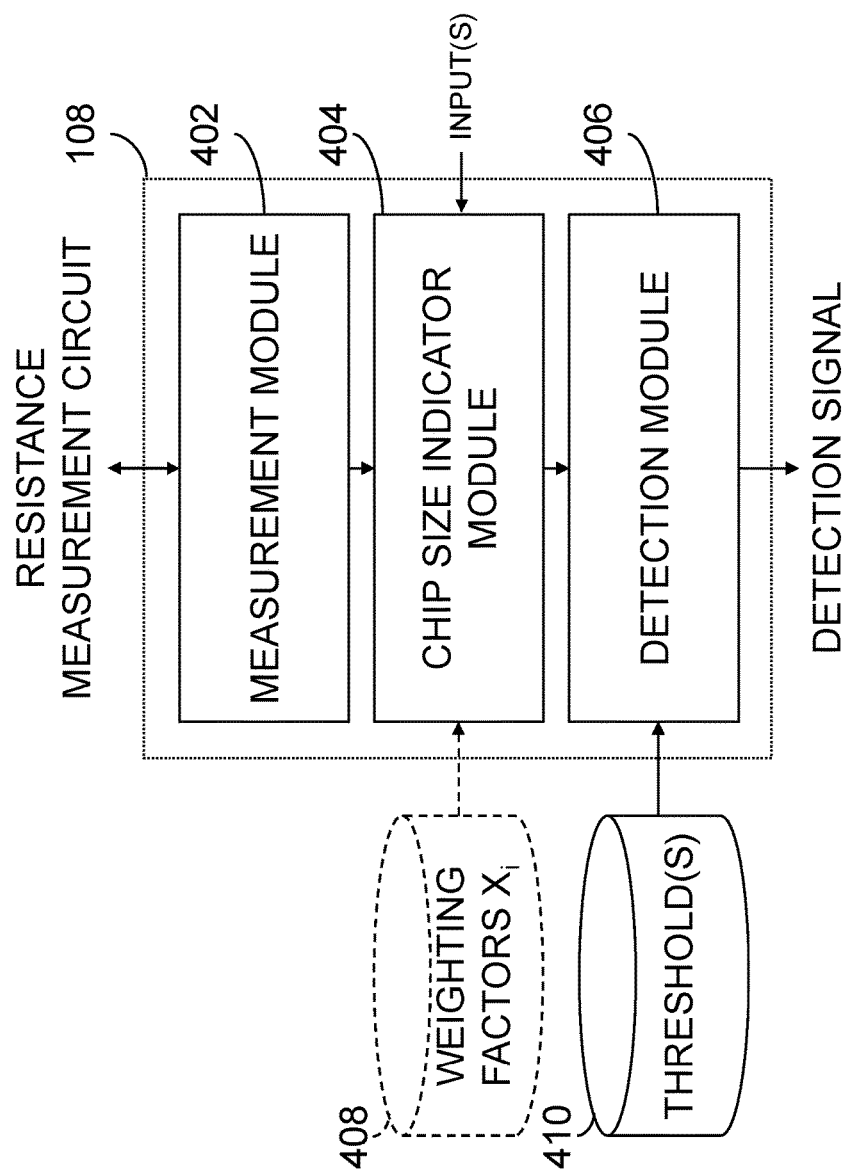
FIG. 4 is a block diagram of an example embodiment of an implementation of the instructions stored on the computing device of FIG. 3.

FIG. 4 is a block diagram of an example embodiment of an implementation of the instructions 306 stored in the memory 304 of the computer 108. As depicted, a measurement module 402, a chip size indicator module 404 and a detection module 406 embody the instructions 306 shown in FIG. 3.

In this embodiment, the measurement module 402 is configured to instruct the resistance measurement circuit 106 to apply the excitation currents $I_i$ and to receive the resistance values $R_i$ and/or voltage values $V_i$ measured by the resistance measurement circuit 106. Once received, the excitation currents $I_i$, the resistance values $R_i$ and the inputs are provided to the chip size indicator module 404.

The chip size indicator module 404 is configured to receive the excitation currents $I_i$ and the resistance values $R_i$ from the measurement module 402, to access weighting factors $X_i$, if necessary, and to determine the chip size indication Y from the resistance values $R_i$. The chip size indicator module 404 can be coupled to a first database 408 storing one or more sets of weighting factors $X_i$. The chip size indicator module 404 can also be configured to receive one or more inputs from the aircraft engine, the aircraft and/or any suitable remote device. Examples of such input includes comprise a type of the aircraft engine, an oil type, an oil flow rate, a rotational speed of the aircraft engine, a capture rate of the magnetic chip detector, a size or quantity of the chip to detect or any combination thereof. In some embodiments, the input(s) can be used to select the weighting factors $X_i$ and/or the threshold $Y_{thres}$. In some embodiments, the input can comprise instructions to weight some of the weighting factors $X_i$ up or down. Once the chip size indication Y is determined, the chip size indication Y is provided to the detection module 406.

The detection module 406 is configured to receive the chip size indication Y from the chip size indicator module 404 and to compare the chip size indication Y to a given threshold $Y_{thres}$. A chip is detected in the fluid when the chip size indication Y exceeds the threshold $Y_{thres}$. When a chip in the fluid is detected, the detection module 406 can be configured to output a detection signal comprising a warning.

The detection module 406 can be coupled to a second database 410 storing one or more thresholds $Y_{thres}$ and accessible by the detection module 406. For instance, the threshold $Y_{thres}$ can be stored on the second database 410. Previously issued warnings can be stored on the second database 410 and form history data representative of the evolution of the chip size indication Y across the gap of the magnetic chip detector 102 over time. The output of the resistance measurement circuit 106 can thus be monitored continuously by the computer 108.

The databases 408 and 410 can be provided locally to the computer 108, or remotely therefrom (e.g., from a database of an aircraft computer or remotely from the aircraft). In some embodiments, the first and second databases 408 and 410 are provided in the form of a single database accessible by the chip size indicator module 404 and by the detection module 406. In addition, although shown as separate from the engine computer 108, the databases 408 and 410 can be integrated therewith. For instance, the databases 408 and 410 can correspond to the memory 304 of the computer 108.

The above description is meant to be exemplary only, and one skilled in the art will recognize that changes may be made to the embodiments described without departing from the scope of the invention disclosed. For example, the methods and systems described therein are applicable to any type of commercial or military aircraft engines having a computer or more specifically an engine computer. Further, at least a first and a second chip detection systems can be mounted to a same engine and be operated as a network of chip detection systems. In this case, a first chip size indication $Y_1$ and a second chip size indication $Y_2$ can be used to detect chips across a corresponding gap of the first and second chip detection systems. In this embodiment, each one of the first and second chip detection systems can have a dedicated resistance measurement circuit. However, in some other embodiments, the first and second chip detection systems are connected to a single resistance measurement circuit via electrical switches so that the computer can detect chips in corresponding chip detection systems by actuating the electrical switches accordingly. Such monitoring can be performed in a pre-determined manner, or in a random or pseudo-random manner, and the monitoring can be performed more frequently for magnetic chip detectors located at key locations of the fluid system than for magnetic chip detectors at non-key locations of the fluid system. Still other modifications which fall within the scope of the present invention will be apparent to those skilled in the art, in light of a review of this disclosure, and such modifications are intended to fall within the appended claims.

The invention claimed is:

1. A method for detecting electrically-conductive particles (chips) in fluid of an aircraft engine, the method comprising:

applying a plurality of excitation currents $I_i$ across a magnetic chip detector mounted to a fluid system of the aircraft engine and measuring a corresponding plurality of resistance values $R_i$, where i is an integer that varies from 1 to N, and where N corresponds to a number of different excitation currents applied across the magnetic chip detector;

determining a chip size indication Y from the plurality of resistance values $R_i$; and detecting a chip in the fluid when the chip size indication Y exceeds a threshold $Y_{thres}$.

2. The method of claim 1, wherein determining the chip size indication Y comprises summing the plurality of resistance values $R_i$ together to obtain the chip size indication Y.

3. The method of claim 2, wherein summing the plurality of resistance values $R_i$ together comprises applying weighting factors $X_i$ to the plurality of resistance values $R_i$ prior to summing the resistance values $R_i$.

4. The method of claim 3, wherein the weighting factors $X_i$ are different for each one of the resistance values $R_i$.

5. The method of claim 3, wherein at least one of the weighting factors $X_i$ is null.

6. The method of claim 3, further comprising receiving an input and selecting the weighting factors $X_i$ based on the input.

7. The method of claim 6, wherein the input depends on at least one of a type of the aircraft engine, an oil type, an oil flow rate, a rotational speed of the aircraft engine, a capture rate of the magnetic chip detector, a target chip size for detection.

8. The method of claim 1, wherein applying the plurality of excitation currents $I_i$ comprises varying a continuous excitation current successively across the plurality of excitation currents $I_i$.

9. The method of claim 8, wherein varying the continuous excitation current successively across the plurality of excitation currents $I_i$ comprises scanning a range of excitation currents at specific intervals.

10. The method of claim 9, wherein applying the plurality of excitation currents $I_i$ comprises repeating said varying a continuous excitation current for a plurality of frequencies.

11. A detection system for an aircraft engine, for electrically-conductive particles (chips), the detection system comprising:

a processing unit; and a non-transitory memory communicatively coupled to the processing unit and comprising computer-readable program instructions executable by the processing unit for:

causing a plurality of excitation currents $I_i$ to be applied across a magnetic chip detector mounted to a fluid system of the aircraft engine and receiving a corresponding plurality of resistance values $R_i$, where i is an integer that varies from 1 to N, and where N corresponds to a number of different excitation currents applied across the magnetic chip detector;

determining a chip size indication Y from the plurality of resistance values $R_i$; and detecting a chip in the fluid when the chip size indication Y exceeds a threshold $Y_{thres}$.

12. The chip detection system of claim 11, wherein determining the chip size indication Y comprises summing the plurality of resistance values $R_i$ together to obtain the chip size indication Y.

13. The chip detection system of claim 12, wherein summing the plurality of resistance values $R_i$ together comprises applying weighting factors $X_i$ to the plurality of resistance values $R_i$ prior to summing the resistance values $R_i$.

14. The chip detection system of claim 13, wherein the weighting factors $X_i$ are different for each one of the resistance values $R_i$.

15. The chip detection system of claim 13, wherein at least one of the weighting factors $X_i$ is null.

16. The chip detection system of claim 13, wherein the program instructions are further executable for receiving an input and selecting the weighting factors $X_i$ based on the input.

17. The chip detection system of claim 11, wherein causing the plurality of excitation currents $I_i$ to be applied comprises varying a continuous excitation current successively across the plurality of excitation currents $I_i$.

18. The chip detection system of claim 17, wherein varying the continuous excitation current successively across the plurality of excitation currents $I_i$ comprises scanning a range of excitation currents at specific intervals.

19. The chip detection system of claim 18, wherein causing the plurality of excitation currents $I_i$ to be applied comprises repeating said varying a continuous excitation current for a plurality of frequencies.

20. The chip detection system of claim 11, further comprising the magnetic chip detector mounted to the fluid system of the aircraft engine and a resistance measurement circuit for applying the plurality of excitation currents $I_i$ across the magnetic chip detector and measuring the corresponding plurality of resistance values $R_i$.

* * * * *